United States Patent
Brost et al.

(10) Patent No.: US 10,390,754 B2
(45) Date of Patent: Aug. 27, 2019

(54) METHOD AND SYSTEM FOR MOTION ESTIMATION MODEL FOR CARDIAC AND RESPIRATORY MOTION COMPENSATION

(71) Applicants: Alexander Benjamin Brost, Erlangen (DE); Sebastian Kaeppler, Erlangen (DE); Martin Ostermeier, Buckenhof (DE); Norbert Strobel, Heroldsbach (DE); Wen Wu, East Windsor, NJ (US); Terrence Chen, Princeton, NJ (US)

(72) Inventors: Alexander Benjamin Brost, Erlangen (DE); Sebastian Kaeppler, Erlangen (DE); Martin Ostermeier, Buckenhof (DE); Norbert Strobel, Heroldsbach (DE); Wen Wu, East Windsor, NJ (US); Terrence Chen, Princeton, NJ (US)

(73) Assignees: Siemens Healthcare GmbH, Erlangen (DE); FRIEDRICH-ALEXANDER-UNIVERSITÄT ERLANGEN-NÜRNBERG, Erlangen (DE)

( * ) Notice: Subject to any disclaimer, the term of this patent is extended or adjusted under 35 U.S.C. 154(b) by 430 days.

(21) Appl. No.: 14/368,833

(22) PCT Filed: Jan. 18, 2013

(86) PCT No.: PCT/US2013/022096
§ 371 (c)(1),
(2) Date: Jun. 26, 2014

(87) PCT Pub. No.: WO2013/112366
PCT Pub. Date: Aug. 1, 2013

(65) Prior Publication Data
US 2014/0378827 A1    Dec. 25, 2014

Related U.S. Application Data

(60) Provisional application No. 61/589,964, filed on Jan. 24, 2012.

(51) Int. Cl.
A61B 5/00    (2006.01)
A61B 5/113    (2006.01)
(Continued)

(52) U.S. Cl.
CPC ............ *A61B 5/4519* (2013.01); *A61B 5/113* (2013.01); *A61B 5/1128* (2013.01); *A61B 34/20* (2016.02);
(Continued)

(58) Field of Classification Search
CPC ............ A61B 18/1492; A61B 19/5244; A61B 2019/5265; A61B 5/1128; A61B 5/113; A61B 34/20; A61B 2034/2065
See application file for complete search history.

(56) References Cited

U.S. PATENT DOCUMENTS

| | | | |
|---|---|---|---|
| 6,473,635 B1 * | 10/2002 | Rasche | A61B 5/06 600/424 |
| 2005/0197568 A1 * | 9/2005 | Vass | G06T 7/0028 600/426 |

(Continued)

OTHER PUBLICATIONS

Alexander Brost, Wen Wu, Martin Koch, Andreas Wimmer, Terrence Chen, Rui Liao, Joachim Hornegger, and Norbert Strobel, Combined Cardiac and Respiratory Motion Compensation for Atrial Fibrillation Ablation Procedures, Med Image Comput Comput Assist Interv. (MICCAI) 2011, pp. 540-547, 14(Pt. 1); 2011.

(Continued)

*Primary Examiner* — Baisakhi Roy

(57) ABSTRACT

A method and system for motion estimation modeling for cardiac and respiratory motion compensation is disclosed. Specifically, a coronary sinus catheter is tracked in a plurality of frames of a fluoroscopic image sequence; and cardiac and respiratory motion of a left atrium is estimated in each of the plurality of frames based on tracking results (Continued)

of the coronary sinus catheter using a trained motion estimation model.

34 Claims, 6 Drawing Sheets

(51) Int. Cl.
*A61B 5/11* (2006.01)
*G06F 7/20* (2006.01)
*G06T 7/20* (2017.01)
*A61B 34/20* (2016.01)
*A61B 18/14* (2006.01)

(52) U.S. Cl.
CPC ............... *G06F 7/20* (2013.01); *G06T 7/20* (2013.01); *A61B 18/1492* (2013.01); *A61B 2034/2065* (2016.02); *G06T 2207/10064* (2013.01); *G06T 2207/20081* (2013.01); *G06T 2207/30021* (2013.01); *G06T 2207/30048* (2013.01)

(56) References Cited

U.S. PATENT DOCUMENTS

| | | | | |
|---|---|---|---|---|
| 2005/0203375 A1* | 9/2005 | Willis | ............... | A61B 5/0422 600/407 |
| 2008/0020362 A1* | 1/2008 | Cotin | ............... | G09B 23/285 434/267 |
| 2009/0062641 A1* | 3/2009 | Barbu | ............... | A61B 19/5244 600/424 |
| 2009/0163800 A1* | 6/2009 | Xu | ............... | A61B 6/12 600/424 |
| 2010/0157041 A1* | 6/2010 | Klaiman | ............... | G06T 7/0022 348/77 |
| 2010/0172555 A1* | 7/2010 | Hasezawa | ............... | G06K 9/00127 382/128 |
| 2010/0172556 A1* | 7/2010 | Cohen | ............... | A61B 6/5217 382/128 |
| 2011/0201915 A1* | 8/2011 | Gogin | ............... | A61B 5/0456 600/407 |
| 2012/0150092 A1* | 6/2012 | McAllister | ............... | A61B 17/11 604/8 |

OTHER PUBLICATIONS

W. Wu, T. Chen, A. Barbu, P. Wang, N. Strobel, S. K. Zhou, and D. Comaniciu, "Learning-based Hypothesis Fusion for Robust Catheter Tracking in 2D X-ray Fluoroscopy," IEEE Conference on Computer Vision and Pattern Recognition (CVPR), 2011, pp. 1097-1104; 2011.

Ma, Yingliang, et al.; "Image-Based Automatic Ablation Point Tagging System with Motion Correction for Cardiac Ablation"; 2011; DE; Jun. 22, 2011.

* cited by examiner

METHOD AND SYSTEM FOR MOTION ESTIMATION MODEL FOR CARDIAC AND RESPIRATORY MOTION COMPENSATION

This application claims the benefit of U.S. Provisional Application No. 61/589,964, filed Jan. 24, 2012, the disclosure of which is herein incorporated by reference.

BACKGROUND OF THE INVENTION

The present invention relates to tracking catheters in fluoroscopic images, and more particularly, to tracking of a plurality of catheters simultaneously in fluoroscopic images using a novel motion compensation method to assist in atrial fibrillation ablation procedures.

Atrial fibrillation (AF) is a rapid, highly irregular heartbeat caused by abnormalities in the electrical signals generated by the atria of the heart. It is the most common cardiac arrhythmia (abnormal heart rhythm) and involves the two upper chambers (atria) of the heart. AF can often be identified by taking a pulse and observing that the heartbeats do not occur at regular intervals. However, a stronger indicator of AF is the absence of P waves on an electrocardiogram, which are normally present when there is a coordinated atrial contraction at the beginning of each heart beat. AF may be treated with medications that either slow the heart rate or revert the heart rhythm back to normal, but this treatment may be difficult and result in complications if a patient has other diseases. Synchronized electrical cardioversion may also be used to convert AF to a normal heart rhythm, but this technique is rarely been used. Surgical and catheter-based AF therapies, such as an ablation procedure, are also commonly used to treat AF.

The identification of triggers that initiate AF within the pulmonary veins (PVs) has led to prevention of AF recurrence by catheter ablation at the site of origin of the trigger. Direct catheter ablation of the triggers was traditionally limited by the infrequency with which AF initiation could be reproducibly triggered during a catheter ablation procedure. To overcome these limitations, an ablation approach was introduced to electrically isolate the PV myocardium. This segmental PV isolation technique involved the sequential identification and ablation of the PV ostium close to the earliest sites of activation of the PV musculature. This typically involved the delivery of radio frequency (RF) energy to 30% to 80% of the circumference of the PVs. The endpoint of this procedure was the electrical isolation of at least three PVs.

Catheter ablation modifies the electrical pathways of the heart in order to treat AF. In order to construct an electrical map of the heart and assist a radiofrequency ablation operation, different catheters, such as ablation, coronary sinus, and circumferential mapping catheters, are inserted in a patient's blood vessels and guided to the heart. The entire operation can be monitored with real-time fluoroscopic images. As the soft-tissue ablation targets inside the heart are not visible within the fluoroscopic images, overlay images generated from computed tomography (CT), magnetic resonance (MR), or C-arm CT can be used during the oblation procedure to facilitate more accurate catheter navigation. However, the clinical value of such overlay images is reduced by cardiac and respiratory motion.

Current technologies concentrate on gating catheter position to a fixed point in time within the cardiac cycle. Respiration effects have not been compensated. The often-advocated static positional reference provides an intermediate accuracy in association with electrocardiogram (ECG) gating. Accurate and fast tracking of catheters during the AF procedures is desirable because such tracking may increase the accuracy of model overlay by compensating respiratory motion as well as cardiac motion.

BRIEF SUMMARY OF THE INVENTION

Embodiments of the present invention provide a system and method for estimation of a position of any device attached to the heart and can be applied to procedures other than electrophysiology procedures such as the atrial fibrillation ablation procedure described in this application if a CS or other linear catheter is used during the procedure.

Particularly, embodiments of the present invention provide a system and method for cardiac and respiratory motion compensation in atrial fibrillation ablation procedures. Embodiments of the present invention utilize a new motion prediction model calculation method to accelerate accurate techniques for tracking moving catheters inside a left atrium during atrial fibrillation (AF) procedures to provide accurate respiratory and cardiac motion information to overlay a heart model to facilitate the AF procedure.

In one embodiment of the present invention, specifically, a first catheter is tracked in a plurality of frames of a fluoroscopic image sequence and cardiac and respiratory motion of at least a portion of a heart is estimated in each of the plurality of frames based on tracking results of the first catheter using a motion estimation model trained based on tracking results of the first catheter and a second catheter tracked in a sequence of training images.

These and other advantages of the invention will be apparent to those of ordinary skill in the art by reference to the following detailed description and the accompanying drawings.

DETAILED DESCRIPTION

Figure 1:
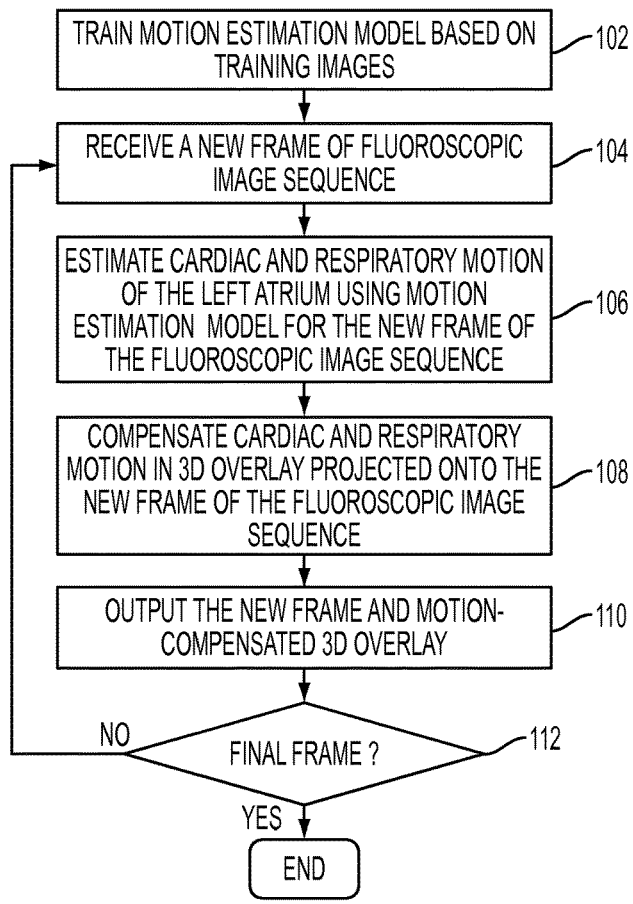
FIG. 1 illustrates a method for cardiac and respiratory motion compensation in atrial fibrillation ablation procedures, according to an embodiment of the present invention.

The present invention relates to a method and system for motion compensation in a fluoroscopic image sequence to assist in atrial fibrillation ablation procedures. A digital image is often composed of digital representations of one or more objects (or shapes). The digital representation of an object is often described herein in terms of identifying and manipulating the object. Such manipulations are virtual manipulations accomplished in the memory or other circuitry/hardware of a computer system. Accordingly, is to be understood that embodiments of the present invention may be performed within a computer system using data stored within the computer system.

In advantageous embodiment of the present invention a first catheter can be a Coronary Sinus (CS) catheter and a second catheter can be a Circumferential Mapping (CM) catheter for an electrophysiology procedure such as the atrial fibrillation ablation procedure. Various approaches for motion compensation based on tracking of the CS or the circumferential mapping catheter have shown to improve the alignment of these overlay images. The downside of using the CS catheter to derive a motion estimate for animating the overlay image is due to the fact that this catheter is outside of the left atrium and close to the left ventricle. Therefore, its movement is strongly influenced by ventricular motion. The circumferential mapping catheter on the other hand has the advantage that it can be placed close to or at the site of ablation. In this case, the calculated circumferential mapping catheter position can be used directly to update the overlay images. Unfortunately, relying on the mapping catheter is not without problems. For example, it may be moved on purpose during the procedure, e.g., to reposition it from one PV to another. Detecting when to stop motion compensation then either requires user interaction or a movement detection algorithm. In addition, if only one transseptal puncture is performed, only one catheter can be inside the left atrium. In this case, the circumferential mapping catheter is brought into the left atrium before and after the ablation of one PV to measure the electrical signals. Thus it may not even be available for motion compensation during the ablation itself. Embodiments of the present invention provide a new method that combines the advantages of the coronary sinus catheter with its continuous presence throughout the procedure along with the accuracy of correlation between the cardiac and respiratory motion of the left atrium and the motion of the mapping catheter. A training phase is used during which both catheters are tracked. The acquired data is then used to train a motion estimation model for capturing the relationship between the position of the CS catheter and the position of the mapping catheter. Finally, the trained estimation model can be used to estimate the cardiac and respiratory motion of the left atrium by observing the CS catheter only in a new image sequence.

FIG. 1 illustrates a method for motion compensation in a fluoroscopic image sequence, according to an embodiment of the present invention. In an embodiment, the method for motion compensation in a fluoroscopic image sequence includes three main phases: a training phase (102), a motion estimation phase (106), and a motion compensation phase (108). As illustrated in FIG. 1, at step 102 a motion estimation model is trained based on a sequence of training images. According to an advantageous implementation, the training images can be frames of a fluoroscopic image sequence. It is to be understood that the fluoroscopic image sequence is a sequence of fluoroscopic (X-ray) images of a patient acquired over a time period. The fluoroscopic image sequence including the training images can be received directly from an X-ray imaging device. It is also possible that the fluoroscopic image sequence including the training images can be received by loading a previously stored fluoroscopic image sequence.

Figure 2:
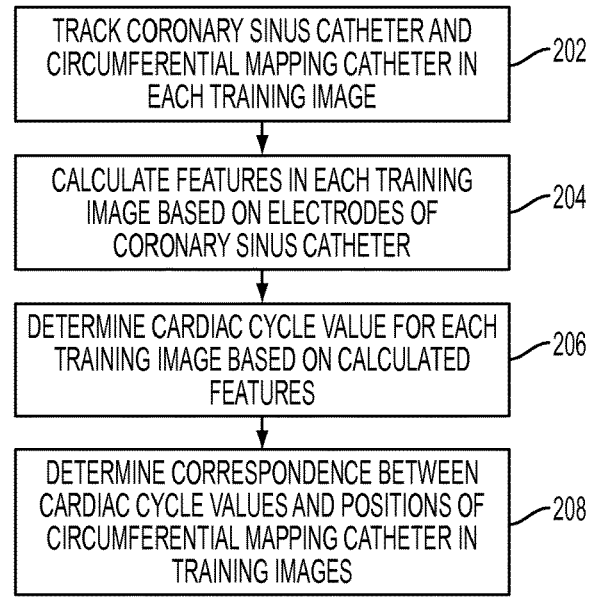
FIG. 2 illustrates an exemplary method for training a motion estimation model, according to an exemplary embodiment of the present invention.

FIG. 2 illustrates an exemplary method for training the motion estimation model, according to an embodiment of the present invention. The method of FIG. 2 can be used to implement step 102 of FIG. 1. At step 202, a coronary sinus (CS) catheter and a circumferential mapping CM catheter are tracked in each training image. In order to track the CS catheter and the CM catheter in the sequence of training image, catheter electrode models for the CS catheter and the CM catheter can be initialized in a first training image in the sequence of training images based on user inputs. The catheter electrode models for the CS catheter and the CM catheter are then tracked in each remaining training image of the sequence of training images. In each remaining training image, candidates of catheter landmarks such as the catheter tip, electrodes and body points are detected for the CS catheter and the CM catheter using trained catheter landmark detectors. For example, catheter tip candidates and electrode candidates can be detected using respective catheter landmark detectors for the CS catheter, and electrode candidates and body point candidates can be detected using respective catheter landmark detectors for the CM catheter. Tracking hypotheses for the catheter electrode models for the CS catheter and the circumferential mapping are generated in each remaining training image, and a probability score is calculated for each tracking hypothesis. For each of the CS catheter and the CM catheter, the catheter electrode model having the highest probability score is selected from the generated tracking hypotheses. Additional details for tracking the CS catheter and the CM catheter are described in U.S. Publication No. 20120070046, entitled "Method and System for Detection and Tracking of Coronary Sinus Catheter Electrodes in Fluoroscopic Images," filed on Sep. 12, 2011, and U.S. patent application Ser. No. 13/622,404, entitled "Method and System for Ablation Catheter and Circumferential Mapping Catheter Tracking in Fluoroscopic Images," filed on Sep. 19, 2012, the disclosures of which are herein incorporated by reference.

In an embodiment, the positions of the electrodes of the CS and the center of the mapping catheter in the training images are stored in a database for later computations. The tracked electrodes of the CS catheter are denoted as $c_i^{(j)} = (u_i^{(j)}, v_i^{(j)})^T$ where $i \in [1, 2, \ldots, N]$, N being the number of electrodes of a catheter and where $j \in [1, M]$, M being the number of images in the training sequence. CS catheters with either four or ten electrodes are typically used during ablation procedures. The center of the mapping catheter in frame j is denoted as $m_j \in R^2$. The image coordinate system is defined by the coordinates u and v. The most distal electrode of the CS catheter is denoted herein as $c_i$ and the most proximal one as $c_N$.

At step 204, a set of features is calculated for each training image based on the electrodes of the CS catheter tracked in each training image. The following features $f_1^{(j)}, \ldots, f_5^{(j)}$ for image j are calculated for all of the training images based on the tracked positions of the electrodes of the CS catheter.

Figure 4A:
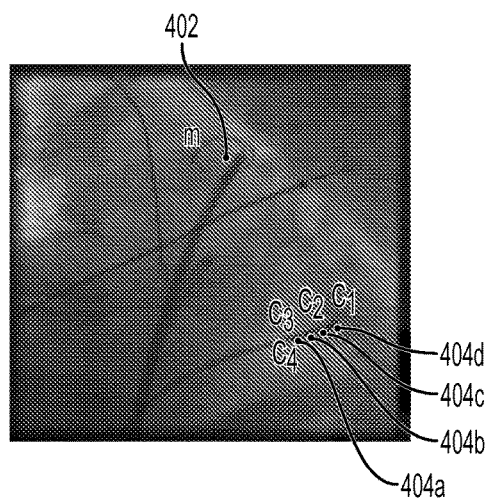
FIG. 4 illustrates exemplary CS and circumferential mapping catheter tracking and feature calculation in a fluoroscopic image, according to an embodiment of the present invention.
Figure 4B:
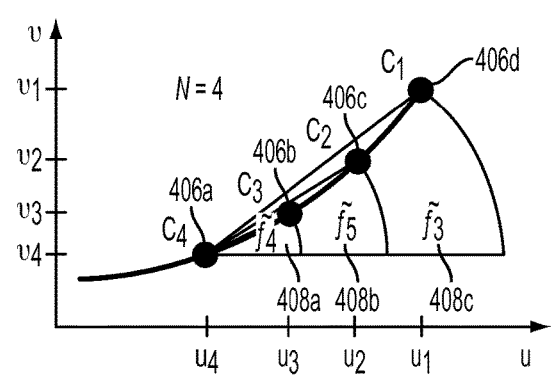

The first feature can be calculated by dividing the u-position of the most distal electrode of the ($c_1$ in FIG. 4(b)) CS catheter by the u-position of the most proximal electrode ($c_4$ in FIGS. 4(a) and 4(b)) of the CS catheter. It is to be understood that the positions are in absolute image coordinates and not related to a reference frame. The first feature can be expressed as:

$$f_1^{(j)} = u_1^{(j)}/u_N^{(j)} \quad (1)$$

The second feature can be calculated by dividing the v-position of the most distal electrode of the CS catheter by the v-position of the most proximal electrode of the CS catheter:

$$f_2^{(j)} = v_1^{(j)}/v_N^{(j)} \qquad (2)$$

The third feature can be determined by determining the angle between the u-axis of the image and the line spanned by the most proximal and most distal electrode of the CS catheter:

$$f_3^{(j)} = \arctan\left(\frac{|v_1^{(j)} - v_N^{(j)}|}{|u_1^{(j)} - u_N^{(j)}|}\right) \qquad (3)$$

The fourth feature can be determined by determining the angle between the u-axis of the image and the line spanned by the most proximal electrode of the CS catheter and the electrode next to the most proximal electrode:

$$f_4^{(j)} = \arctan\left(\frac{|v_{N-1}^{(j)} - v_N^{(j)}|}{|u_{N-1}^{(j)} - u_N^{(j)}|}\right) \qquad (4)$$

The fifth feature can be determined by determining the angle between the u-axis of the image and the line spanned by the most proximal electrode of the CS catheter and the second electrode from the most proximal electrode:

$$f_5^{(j)} = \arctan\left(\frac{|v_{N-2}^{(j)} - v_N^{(j)}|}{|u_{N-2}^{(j)} - u_N^{(j)}|}\right) \qquad (5)$$

The calculated features $f_1^{(j)}, \ldots, f_5^{(j)}$ capture CS catheter rotations and deformations, which are typical for cardiac motion. It is to be noted that CS catheter rotations and deformations are relatively invariant to translation motion, which is characteristically for respiratory motion. As the feature values have different ranges, they are normalized to the range [0, 1] and the resulting features are denoted in vector notation as:

$$f_j = (\hat{f}_1^{(j)}, \hat{f}_2^{(j)}, \hat{f}_3^{(j)}, \hat{f}_4^{(j)}, \hat{f}_5^{(j)})^T \qquad (6)$$

Returning to FIG. 2, at step 206, based on the calculated set of features, a cardiac cycle value is determined for each training image. Although it is possible to use ECG data to determine a cardiac phase for a given frame, this data is not always readily available and its accuracy may be affected by irregularities of the heart beat. Accordingly, in an embodiment of the present invention, the calculation of the cardiac phase is based on a pattern recognition approach. While respiration causes only a slight rotational movement of the heart, the electrodes of the CS catheter show a large relative rotative movement during the cardiac cycle. Such movement due to the cardiac cycle can be captured using the above described a feature set based on the positions of the electrodes of the CS catheter.

FIG. 4 illustrates exemplary CS and circumferential mapping catheter tracking and feature calculation in a fluoroscopic image. Image (a) of FIG. 4 illustrates a plurality of electrodes 404d, 404c, 404b, and 404a (respectively $c_1$, $c_2$, $c_3$, $c_4$) of the CS catheter and the center 402(m) of a circumferential mapping catheter detected in a fluoroscopic image. Image (b) of FIG. 4 illustrates calculation of features $f_3$, $f_4$, and $f_5$ based on the detected positions of electrodes 406a, 406b, 406c, and 406d of the CS catheter.

To reduce the dimensionality of the feature vector calculated for each training image, a principle component analysis can be performed. A mean feature vector for the set of training images is calculated by:

$$\bar{f} = \frac{1}{M}\sum_{j=1}^{M} f_j \qquad (7)$$

A covariance matrix is then calculated by:

$$\sum = \frac{1}{M-1}\sum_{j=1}^{M}(f_j - \bar{f}) \cdot (f_j - \bar{f})^T \qquad (8)$$

Following the calculation of the covariance matrix, a unitless cardiac cycle value for every image in the training sequence is calculated based on the eigenvalues and eigenvectors of $\Sigma$:

$$\mu_j = e_\lambda^T \cdot (f_j - \bar{f}) \qquad (9)$$

where $e_\lambda^T$ is the eigenvector corresponding to the largest eigenvalue of the covariance matrix $\Sigma$. In an embodiment of the present invention, the calculated unitless cardiac cycle value $\mu_j$ for a frame represents the length of the orthogonal projection of the feature vector for that frame onto the first eigenvector.

Figure 5A:
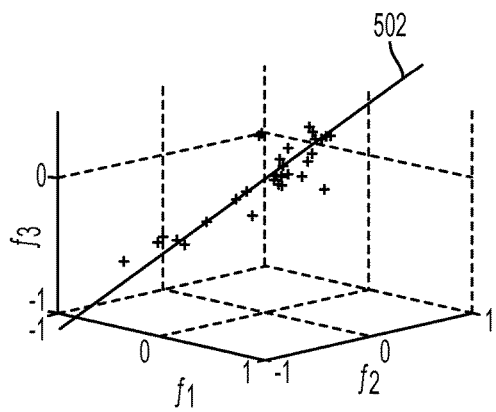
FIG. 5 illustrates an exemplary visualization of the feature space.
Figure 5B:
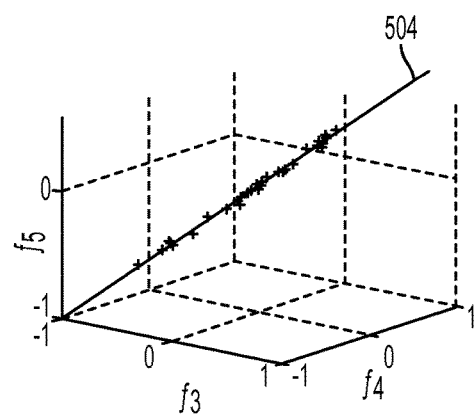

FIG. 5 illustrates the fit of $e_\lambda$ to the features in feature space. Image (a) of FIG. 5 illustrates first three features $f_1$, $f_2$, $f_3$ computed on a training set, and a corresponding principle axis 502. Image (b) of FIG. 5 illustrates last three features $f_3$, $f_4$, $f_5$ computed on the same training set, and the corresponding principle axis 504.

At step 208, a correspondence is determined between the cardiac cycle values and positions of the CM catheter in the training images. In particular, once the cardiac cycle value $\mu_j$ is calculated for each frame, a correspondence between the calculated cardiac cycle value $\mu_j$ and the stored position of the mapping catheter $m_j$ is established and can be used to predict the position of the circumferential mapping catheter based on the cardiac cycle value $\mu_j \to m_j$.

Figure 6:
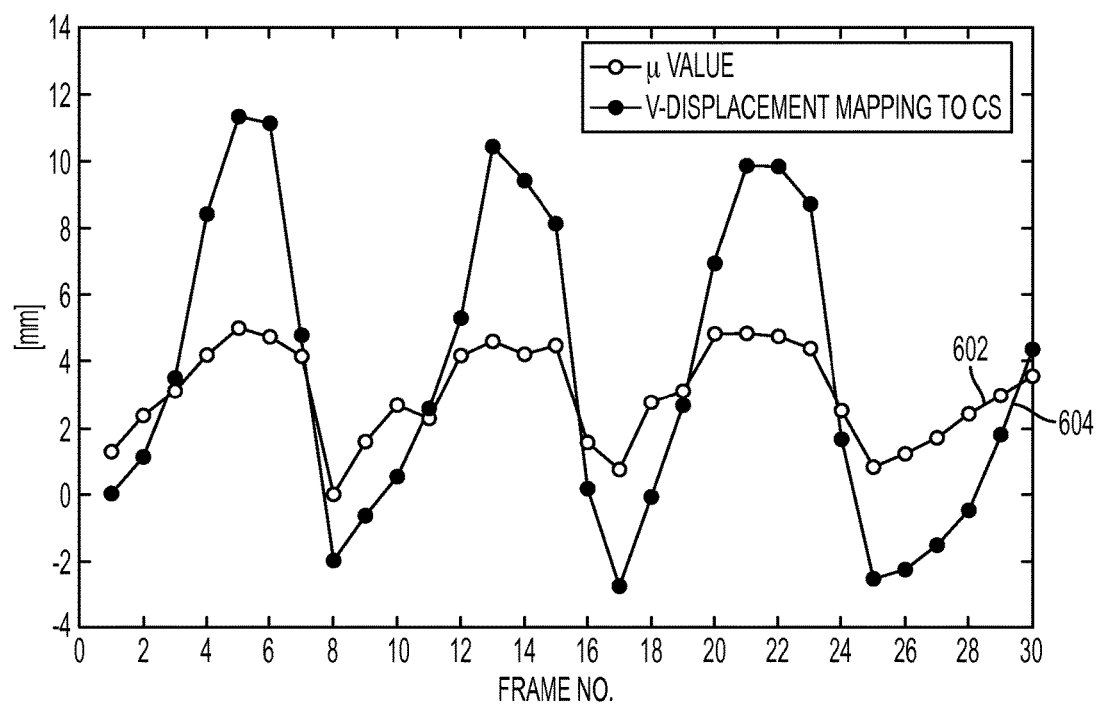
FIG. 6 illustrates a correspondence between calculated cardiac cycle values and the displacement between the proximal electrode of the CS and the center of the circumferential mapping catheter in v-direction in a sequence of training images.

FIG. 6 illustrates a correspondence between the cardiac cycle values and tracked positions of the CM catheter in a sequence of training images. In particular, the illustrated correspondence is between a cardiac cycle values (line 602) determined for a training set and the displacement (line 604) between the proximal electrode of the CS catheter and the center of the CM catheter in v-direction (vertical axis of FIG. 6 measured in millimeters) with respect to a reference frame.

Returning to FIG. 1, at step 104, a new frame of fluoroscopic image sequence is received. The fluoroscopic image sequence is a sequence of fluoroscopic (X-ray) images acquired over a time period. The fluoroscopic image sequence can be received directly from an X-ray imaging device in real-time during atrial fibrillation procedure. In an advantageous implementation, the fluoroscopic image sequence can be a plurality of images of the same patient as the sequence of the training images. The new frame of the fluoroscopic image sequence can be a later frame of the same fluoroscopic image sequence as the sequence of training images or it can be part of a separate fluoroscopic image sequence initiated at a later time.

At step 106, cardiac and respiratory motion of the left atrium is estimated using the motion estimation model based on tracking results of the CSC in the new frame.

Figure 3:
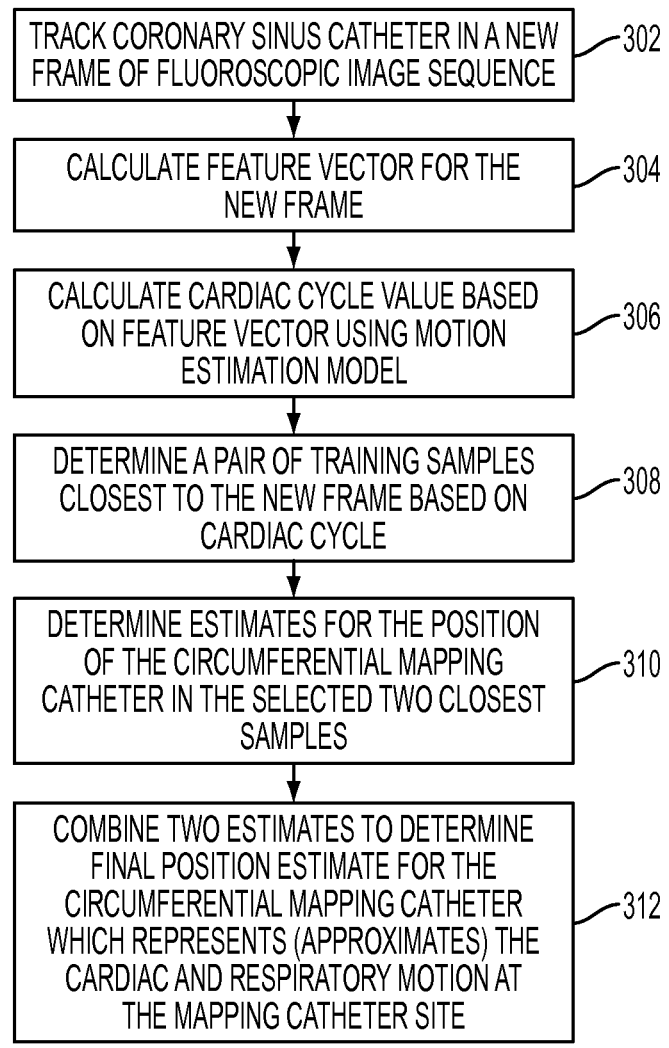
FIG. 3 illustrates a method for estimating a cardiac and respiratory motion of the left atrium in a fluoroscopic image using the learned motion estimation model, according to an embodiment of the present invention.

FIG. 3 illustrates a method for estimating cardiac and respiratory motion of the left atrium, according to an embodiment of the present invention. The method of FIG. 3 can be utilized to implement step 106 of FIG. 1.

At step 302, a CS catheter is tracked in the new frame of fluoroscopic image sequence. The CS catheter can be tracked by tracking the catheter electrode model for the CS catheter in the new frame, using the method described above in connection with step 202 of FIG. 2.

At step 304, a feature vector $f_{new}$ for the new frame of the fluoroscopic image sequence is determined based on the electrode locations of the CS catheter tracked in the new frame. The feature vector $f_{new}$ is determined as shown in equation (6) above by calculating the features based on the tracked CS electrodes in the new frame using equations (1)-(5), and normalizing the resulting features.

At step 306, a cycle value is calculated for the new frame using the trained motion estimation model. In an embodiment of the present invention, the cycle value at the new frame is calculated as:

$$\mu_{new} = e_\lambda^T \cdot (f_{new} - \bar{f}), \tag{10}$$

where $\bar{f}$ and $e_\lambda$ are learned from the training image. The $\bar{f}$ is the mean feature vector, calculated by equation (7) above, calculated from the training images and $e_\lambda$ is the largest eigenvalue of the covariance matrix calculated from the training images in equation (8) above.

At step 308, a pair of training images closest to a new image of the fluoroscopic image sequence with respect to the cardiac phase is determined. In an embodiment of the present invention, one training image, denoted as $\beta$, is earlier in the cardiac cycle than the new image, while the other training image, denoted as $\gamma$, is later in the cardiac cycle than the new image. The pair of training images closest to a current image of the fluoroscopic image sequence can be determined by solving a minimization problem in order to reduce the effect of errors in the calculation of the heart cycle:

$$\beta = \underset{\substack{j \\ \mu_j < \mu_{new}}}{\operatorname{argmin}} (1 + |\mu_j - \mu_{new}|)^2 + \alpha \cdot (u_N^{(j)} - u_N^{(new)})^2 \tag{11}$$

$$\gamma = \underset{\substack{j \\ \mu_j \geq \mu_{new}}}{\operatorname{argmin}} (1 + |\mu_j - \mu_{new}|)^2 + \alpha \cdot (u_N^{(j)} - u_N^{(new)})^2$$

The position of the most proximal electrode in u-direction, $u_N^{(new)}$, is used for regularization. The idea behind the term "regularization" is to reduce the effect of errors in the calculation of the heart cycle, which may, for example, arise from slight inaccuracies in the catheter tracking. The cardiac cycle values $\mu_\beta$ and $\mu_\gamma$ correspond to the two samples closest to the new frame with respect to the observed cardiac cycle value $\mu_{new}$.

At step 310, estimates for positions of the CMC are determined based on the pair of training images. Using values $\mu_\beta$ and $\mu_\gamma$, two estimates for the position of the circumferential mapping catheter are calculated as:

$$\hat{m}_{new,\beta} = m_\beta + (c_N^{(new)} - c_N^{(\beta)}) \tag{12}$$

$$\hat{m}_{new,\gamma} = m_\gamma + (c_N^{(new)} - c_N^{(\gamma)}) \tag{13}$$

The difference terms in the equations for calculation of two estimates for the position of the circumferential mapping catheter provide the compensation for respiratory motion. For two images in the same cardiac phase, the assumption is that any remaining motion must be due to respiration. Also, assuming that the CS catheter and the mapping catheter are equally affected by respiratory motion, the difference vector between the proximal electrodes of the CS catheter in the two images is applied to the estimate of the position of the mapping catheter at the target motion estimation site although the mapping catheter is not present in the new image. The proximal electrode is selected because it shows the least intra-cardiac motion with respect to the mapping catheter.

At step 312, a final estimate of the position of the CM catheter is determined based on proximal electrodes of the CS catheter and the determined estimates for the position of the CM catheter. In order to calculate the final estimate, the two estimates for the positions of the circumferential mapping catheter are combined:

$$\hat{m}_{new} = \phi \cdot \hat{m}_{new,\beta} + (1-\phi) \cdot \hat{m}_{new,\gamma}, \tag{14}$$

where the scaling value $\phi$ between the two estimates is calculated as:

$$\phi = \frac{|\mu_\gamma - \mu_{new}|}{|\mu_\gamma - \mu_\beta|} \tag{15}$$

In an embodiment of the present invention, in case of high acquisition frame rates ≥15 frames-per-second, a temporal low pass filter can be applied:

$$\hat{m}'_{new} = \delta \cdot \hat{m}_{new} + (1-\delta) \cdot \hat{m}_{new-1} \tag{16}$$

because the motion of the heart is smooth in high frame rate image sequences. The position of the CM catheter is an estimate based on the tracked CM catheter in the training frames, not necessarily an actual detection of a current location of the CM catheter. This position can be estimated even if CM catheter is no longer positioned in the location in the left atrium where the training images are collected. The motion of this estimated position of the CM catheter between frames provides an estimate of the motion of the left atrium due to cardiac and respiratory motion.

Returning to FIG. 1, at step 108, cardiac and respiratory motion can be compensated in a three-dimensional overlay projected onto the new frame of fluoroscopic image sequence. Motion is provided by the current estimated position of the CM catheter versus the position of the CM catheter in a reference frame. A 3D overlay is adjusted based on the estimated motion.

At step 110, the new frame as the motion-compensated 3D overlay is output and a compensated motion in 3D overlay is projected onto each frame of fluoroscopic image sequence. It is to be understood that the motion-compensated 3D overlay is output to a suitable output device and/or stored in a database for future processing or analysis. For example, the new frame and motion-compensated 3D overlay may be displayed by a display device of a computer system. The new frame and motion-compensated 3D overlay can also be displayed in real-time during atrium fibrillation procedure.

At step 112, a determination is made whether the new frame is a last frame of fluoroscopic image sequence. If a determination is made that the new frame is the last frame, the method of FIG. 1 ends. If, however, if a determination is made that the new frame is not the last frame of fluoroscopic image sequence, the method of FIG. 1 loops to step 104 in which a subsequently new frame is received and then processed through steps 106-112. It is to be understood that steps 104-112 of FIG. 1 may be repeated until a determination is made that the new image is the last image of fluoroscopic image sequence.

Figure 7A:
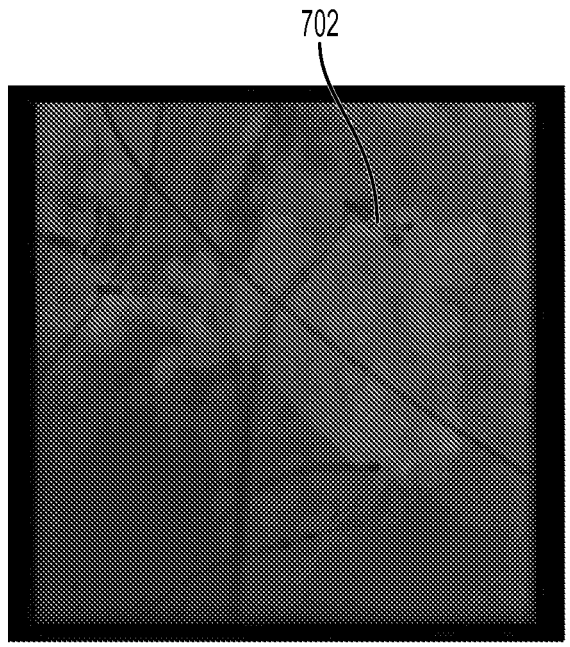
FIG. 7 illustrates exemplary motion compensation results.
Figure 7B:
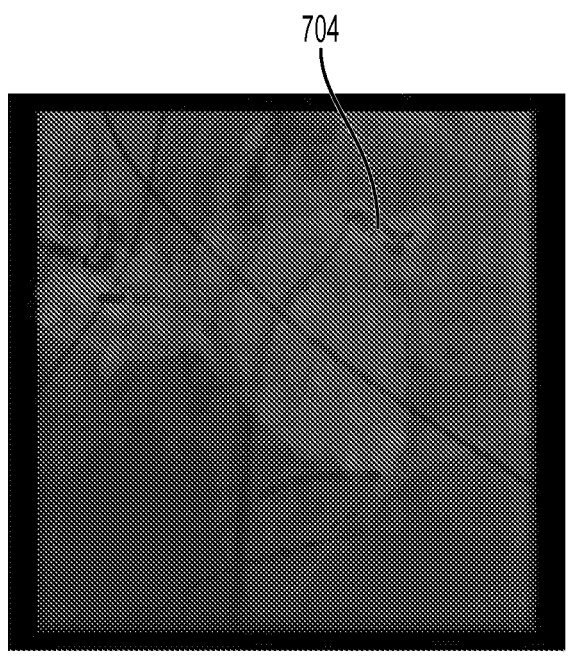

FIG. 7 illustrates exemplary motion compensation results. Specifically, image (a) shows an exemplary frame with an overlay 702 shown without motion compensation. Image (b) shows same exemplary frame in which overlay 704 is shown with motion compensation.

Although the methods of FIGS. 1, 2, and 3 are described above as being implemented using a CS catheter and a CM catheter to estimate motion of the left atrium, the present invention is not limited thereto. The methods described above can be implemented using by tracking any first catheter and estimating motion of a portion of the heart based on an motion estimation model trained based on detections of the first catheter and a second catheter, which is located at the portion of the heart, in a sequence of training images. In various advantageous embodiments, any type of linear catheter, of which the CS catheter is one example, can be used as the first catheter, and a CM catheter or an ablation catheter can be used as the second catheter, but the present invention is not limited thereto.

The methods described above can be implemented to estimate and compensate motion in original resolution, half resolution, or multi-resolution. The above-described methods can be also utilized in mono-plane or bi-plane fluoroscopic image sequences.

Figure 8:
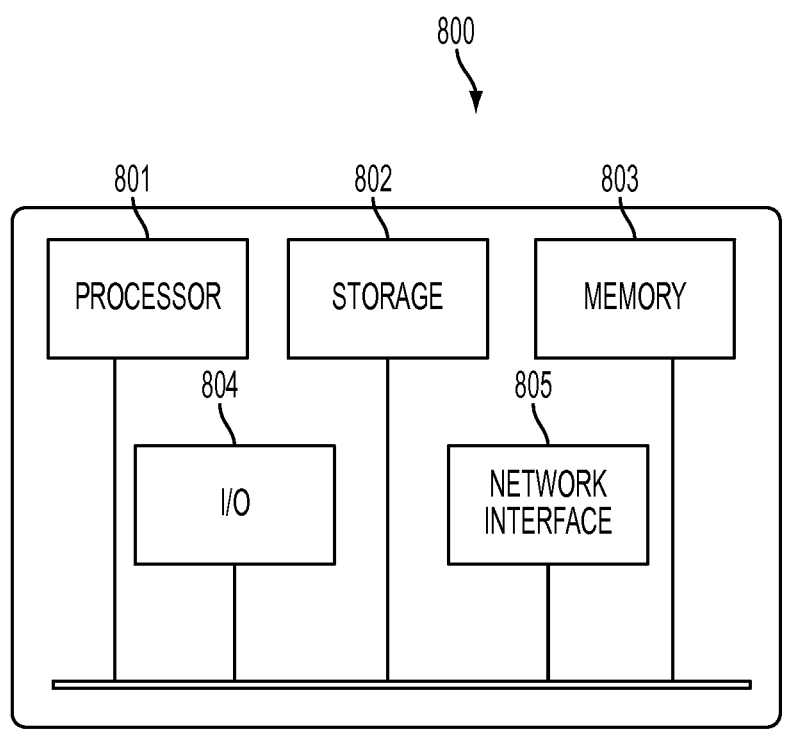
FIG. 8 illustrates a high-level block diagram of a computer capable of implementing the present invention.

The above-described methods for cardiac motion estimation and compensation in a fluoroscopic image sequence may be implemented on a computer using well-known computer processors, memory units, storage devices, computer software, and other components. A high level block diagram of such a computer is illustrated in FIG. 8. Computer 802 contains a processor 804, which controls the overall operation of the computer 802 by executing computer program instructions which define such operation. The processor 804 may include a Central Processing Unit (CPU) and a Graphics Processing Unit (GPU). The computer program instructions may be stored in a storage device 802, or other computer readable medium, (e.g., magnetic disk) and loaded into memory 810 when execution of the computer program instructions is desired. Thus, all method steps described above, including the method steps illustrated in FIGS. 1, 2, and 3 may be defined by the computer program instructions stored in the memory 810 and/or storage 812 and controlled by the processor 804 executing the computer program instructions. An image acquisition device 820, such as an X-ray imaging device, can be connected to the computer 802 to input fluoroscopic image sequences to the computer 802. It is possible to implement the image acquisition device 820 and the computer 802 as one device. It is also possible that the image acquisition device 820 and the computer 802 communicate wirelessly through a network. The computer 802 also includes one or more network interfaces 806 for communicating with other devices via a network. The computer 802 also includes other input/output devices 808 that enable user interaction with the computer 802 (e.g., display, keyboard, mouse, speakers, buttons, etc.) One skilled in the art will recognize that an implementation of an actual computer could contain other components as well, and that FIG. 8 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
   training a motion estimation model based on tracked electrodes of a first catheter and a tracked second catheter in a sequence of training images, wherein training the motion estimation model comprises:
   detecting the electrodes of the first catheter and the second catheter in each training image sequence of training images;
   calculating features in each training image based on locations of the electrodes of the first catheter;
   determining a cardiac cycle value for each training image based on the calculated features; and
   determining a correspondence between the cardiac cycle values and positions of the second catheter in the training images;
   tracking the first catheter in a plurality of frames of a fluoroscopic image sequence; and
   estimating cardiac and respiratory motion of a portion of a heart in each of the plurality of frames based on a position of the second catheter determined from the tracking of the first catheter using the trained motion estimation model, the trained motion estimation model trained based on tracking the first catheter and the second catheter in the sequence of training images.

2. The method of claim 1, wherein the sequence of training images is of same patient as the fluoroscopic image sequence.

3. The method of claim 1, wherein the sequence of training images is a number of frames of the fluoroscopic image sequence prior to the plurality of frames of the fluoroscopic image sequence.

4. The method of claim 1, wherein calculating features in each image comprises:
   for each training image j:
   calculating a first of the plurality of features as:
   $f_1^{(j)} = u_1^{(j)}/u_N^{(j)}$;
   calculating a second of the plurality of features as:
   $f_2^{(j)} = v_1^{(j)}/v_N^{(j)}$;
   calculating a third of the plurality of features as:

$$f_3^{(j)} = \arctan\left(\frac{|v_1^{(j)} - v_N^{(j)}|}{|u_1^{(j)} - u_N^{(j)}|}\right);$$

calculating a fourth of the plurality of features as $$f_4^{(j)} = \arctan\left(\frac{|v_{N-1}^{(j)} - v_N^{(j)}|}{|u_{N-1}^{(j)} - u_N^{(j)}|}\right);$$

and calculating a fifth of the plurality of features as:

$$f_5^{(j)} = \arctan\left(\frac{|v_{N-2}^{(j)} - v_N^{(j)}|}{|u_{N-2}^{(j)} - u_N^{(j)}|}\right),$$

wherein $c_1$ is a most distal electrode of the first catheter and $c_N$ is a most proximate electrode of the first catheter, where $c_1, \ldots, c_N$ denote the electrodes of the first catheter, and $(u_i^{(j)}, v_i^{(j)})$ denote coordinates of $c_i$ in training image.

5. The method of claim 4, wherein determining a cardiac cycle value for each training image comprises:
calculating a new feature vector as:

$$\bar{f} = \frac{1}{M}\sum_{j=1}^{M} f_j,$$

where $f_j = (\tilde{f}_1^{(j)}, \tilde{f}_2^{(j)}, \tilde{f}_3^{(j)}, \tilde{f}_4^{(j)}, \tilde{f}_5^{(j)})^T$ is a normalized feature of frame j;
calculating a covariance matrix as:

$$\Sigma = \frac{1}{M-1}\sum_{j=1}^{M}(f_j - \bar{f})\cdot(f_j - \bar{f})^T;$$

and
calculating the cardiac cycle value for each frame as:
$\mu_j = e_\lambda^T \cdot (f_j - \bar{f})$, where $e_\lambda$ a largest eigenvalue of the covariance matrix $\Sigma$.

6. The method of claim 1, further comprising:
compensating for the estimated cardiac and respiratory motion of the portion of the heart in a 3D overlay projected onto each of the plurality of frames of the fluoroscopic image sequence.

7. The method of claim 1, wherein the first catheter is a linear catheter and the second catheter is located at the portion of the heart in the sequence of training images.

8. The method of claim 7, wherein the second catheter is one of an circumferential mapping catheter or an ablation catheter.

9. The method of claim 1, wherein the first catheter is a coronary sinus catheter, the second catheter is a circumferential mapping catheter, and the portion of the heart is a left atrium.

10. A method of comprising:
tracking a first catheter in a plurality of frames of a fluoroscopic image sequence; and
estimating cardiac and respiratory motion of a portion of a heart in each of the plurality of frames based on a position of a second catheter determined from the tracking of the first catheter using a trained motion estimation model, the trained motion estimation model trained based on tracking the first catheter and the second catheter in a sequence of training images, wherein the step of estimating cardiac and respiratory motion comprises, for each of the plurality of frames of the fluoroscopic image sequence:
tracking the electrodes of the first catheter in the frame;
calculating a feature vector based on the tracked electrodes of the first catheter;
calculating a cardiac cycle value based on the feature vector using the trained motion estimation model;
determining a pair of training samples closest to the frame based on the calculated cardiac cycle value;
determining estimates for a position of the second catheter in the frame from the pair of training samples; and
combining the estimates to determine a final estimate for the position of the second catheter.

11. The method of claim 10, where calculating a cardiac cycle value comprises:
calculating the cardiac cycle value as:
$\mu_{new} = e_\lambda^T \cdot (f_{new} - \bar{f})$, wherein $f_{new}$ is the feature vector calculated from a current frame, $\bar{f}$ is a mean feature vector learned from a sequence of training Images, and $e_\lambda^T$ is an eigenvector corresponding to a largest eigenvalue of a covariance matrix.

12. The method of claim 10, wherein determining a pair of training samples closest to the frame comprises:
determining a pair of training samples as:

$$\beta = \underset{\substack{j \\ \mu_j < \mu_{new}}}{\operatorname{argmin}}(1 + |\mu_j - \mu_{new}|)^2 + \alpha \cdot (u_N^{(j)} - u_N^{(new)})^2$$

where $$\gamma = \underset{\substack{j \\ \mu_j \geq \mu_{new}}}{\operatorname{argmin}}(1 + |\mu_j - \mu_{new}|)^2 + \alpha \cdot (u_N^{(j)} - u_N^{(new)})^2,$$

$\mu_j$ and $\mu_{new}$ are cardiac cycle values,
$u_N^{(new)}$ is a position of most proximal electrodes in to u-direction, and
$\alpha$ is an empirical value.

13. The method of claim 12, wherein determining estimates comprises:

$\hat{m}_{new,\beta} = m_\beta + (c_N^{(new)} - c_N^{(\beta)})$; and $\hat{m}_{new,\gamma} = m_\gamma + (c_N^{(new)} - c_N^{(\gamma)})$.

14. The method of claim 10, wherein combining the estimates to determine a final estimate for the position of the second catheter comprises:

$\hat{m}_{new} = \phi \cdot \hat{m}_{new,\beta} + (1-\phi) \cdot \hat{m}_{new,\gamma}$, wherein the scaling value $\phi$ between the two estimates is calculated as:

$$\phi = \frac{|\mu_\gamma - \mu_{new}|}{|\mu_\gamma - \mu_\beta|}.$$

15. The method of claim 10, further comprising:
compensating for the estimated cardiac and respiratory motion of the portion of the heart in a 3D overlay projected onto each of the plurality of frames of the fluoroscopic image sequence.

16. The method of claim 10, wherein the first catheter is a linear catheter and the second catheter is located at the portion of the heart in the sequence of training images.

17. The method of claim 16, wherein the second catheter is one of an circumferential mapping catheter or an ablation catheter.

18. The method of claim 10, wherein the first catheter is a coronary sinus catheter, the second catheter is a circumferential mapping catheter, and the portion of the heart is a left atrium.

19. An apparatus comprising:
means for training a motion estimation model based on tracked electrodes of a first catheter and a tracked second catheter in a sequence of training images, wherein the means for training the motion estimation model comprises:
  means for detecting the electrodes of the first catheter and the second catheter in each training image sequence of training images;
  means for calculating features in each training image based on locations of the electrodes of the first catheter;
  means for determining a cardiac cycle value for each training image based on the calculated features; and
  means for determining a correspondence between the cardiac cycle values and positions of the second catheter in the training images;
means for tracking the first catheter in a plurality of frames of a fluoroscopic image sequences; and
means for estimating cardiac and respiratory motion of at least a portion of a heart in each of the plurality of frames based on a position of the second catheter determined from the tracking of the first catheter using the trained motion estimation model, the trained motion estimation model trained based on tracking the first catheter and the second catheter in the sequence of training images.

20. The apparatus of claim 19, further comprising:
means for compensating for the estimated cardiac and respiratory motion of the at least the portion of the heart in a 3D overlay projected onto each of the plurality of frames of the fluoroscopic image sequence.

21. An apparatus comprising:
means for tracking a first catheter in a plurality of frames of a fluoroscopic image sequence; and
means for estimating cardiac and respiratory motion of at least a portion of a heart in each of the plurality of frames based on a position of a second catheter determined from the tracking of the first catheter using a trained motion estimation model, the trained motion estimation model trained based on tracking the first catheter and the second catheter in a sequence of training images, wherein the means for estimating cardiac and respiratory motion comprises, for each of the plurality of frames of the fluoroscopic image sequence:
  means for tracking electrodes of the first catheter in the frame;
  means for calculating a feature vector based on the tracked electrodes of the first catheter;
  means for calculating a cardiac cycle value based on the feature vector using the trained motion estimation model;
  means for determining a pair of training samples closest to the frame based on the calculated cardiac cycle value;
  means for determining estimates for the position of the second catheter in the frame from the pair of training samples; and
  means for combining the estimates to determine a final estimate for the position of the second catheter.

22. The apparatus of claim 21, further comprising:
means for compensating for the estimated cardiac and respiratory motion of the at least the portion of the heart in a 3D overlay projected onto each of the plurality of frames of the fluoroscopic image sequence.

23. A non-transitory computer readable medium encoded with computer executable instructions for defining steps comprising:
training a motion estimation model based on tracked electrodes of a first catheter and a tracked second catheter in a sequence of training images, wherein training the motion estimation model comprises:
  detecting the electrodes of the first catheter and the second catheter in each training image sequence of training images;
  calculating features in each training image based on locations of the electrodes of the first catheter;
  determining a cardiac cycle value for each training image based on the calculated features; and
  determining a correspondence between the cardiac cycle values and positions of the second catheter in the training images;
tracking the first catheter in a plurality of frames of a fluoroscopic image sequence; and
estimating cardiac and respiratory motion of at least a portion of a heart in each of the plurality of frames based on a position of the second catheter determined from the tracking of the first catheter using the trained motion estimation model, the trained motion estimation model trained based on tracking the first catheter and the second catheter in the sequence of training images.

24. The non-transitory computer readable medium of claim 23, wherein the sequence of training images is of same patient as the fluoroscopic image sequence.

25. The non-transitory computer readable medium of claim 23, wherein the sequence of training images is a number of frames of the fluoroscopic image sequence prior to the plurality of frames of the fluoroscopic image sequence.

26. The non-transitory computer readable medium of claim 23, wherein calculating features in each image comprises:
for each training image j:
  calculating a first of the features as: $f_1^{(j)} = u_1^{(j)}/u_N^{(j)}$;
  calculating a second of the features as: $f_2^{(j)} = v_1^{(j)}/v_N^{(j)}$;
  calculating a third of the features as:

$$f_3^{(j)} = \arctan\left(\frac{|v_1^{(j)} - v_N^{(j)}|}{|u_1^{(j)} - u_N^{(j)}|}\right);$$

calculating a fourth of the features as $$f_4^{(j)} = \arctan\left(\frac{|v_{N-1}^{(j)} - v_N^{(j)}|}{|u_{N-1}^{(j)} - u_N^{(j)}|}\right);$$

and
  calculating a fifth of the features as:

$$f_5^{(j)} = \arctan\left(\frac{|v_{N-2}^{(j)} - v_N^{(j)}|}{|u_{N-2}^{(j)} - u_N^{(j)}|}\right),$$

wherein $c_1$ is a most distal electrode of the first catheter and $c_N$ is a most proximate electrode of the first catheter, where $c_1, \ldots, c_N$ denote the electrodes of the first catheter, and $(u_i^{(j)}, v_i^{(j)})$ denote coordinates of $c_i$ in training image.

27. The non-transitory computer readable medium of claim 26, wherein determining a cardiac cycle value for each training image comprises:
calculating a new feature vector as:

$$\bar{f} = \frac{1}{M}\sum_{j=1}^{M} f_j,$$

where $f_j = (\tilde{f}_1^{(j)}, \tilde{f}_2^{(j)}, \tilde{f}_3^{(j)}, \tilde{f}_4^{(j)}, \tilde{f}_5^{(j)})^T$ is a normalized feature of frame j;
calculating a covariance matrix as:

$$\sum = \frac{1}{M-1}\sum_{j=1}^{M}(f_j - \bar{f})\cdot(f_j - \bar{f})^T;$$

and
calculating the cardiac cycle value for each frame as: $\mu_j = e_\lambda^T \cdot (f_j - \bar{f})$, where $e_\lambda$ is a largest eigenvalue of the covariance matrix $\Sigma$.

28. The non-transitory computer readable medium of claim 23, further comprising:
compensating for the estimated cardiac and respiratory motion of the at least the portion of the heart in a 3D overlay projected onto each of the plurality of frames of the fluoroscopic image sequence.

29. A The non-transitory computer readable medium encoded with computer executable instructions for defining steps comprising:
tracking a first catheter in a plurality of frames of a fluoroscopic image sequence; and
estimating cardiac and respiratory motion of at least a portion of a heart in each of the plurality of frames based on a position of a second catheter determined from the tracking of the first catheter using a trained motion estimation model, the trained motion estimation model trained based on tracking the first catheter and the second catheter in a sequence of training images, wherein the step of estimating cardiac and respiratory motion comprises, for each of the plurality of frames of the fluoroscopic image sequence:
tracking electrodes of the first catheter in the frame;
calculating a feature vector based on the tracked electrodes of the first catheter;
calculating a cardiac cycle value based on the feature vector using the trained motion estimation model;
determining a pair of training samples closest to the frame based on the calculated cardiac cycle value;
determining estimates for the position of the second catheter in the frame from the pair of training samples; and
combining the estimates to determine a final estimate for the position of the second catheter.

30. The non-transitory computer readable medium of claim 29, where calculating a cardiac cycle value comprises:
calculating the cardiac cycle value as:
$\mu_{new} = e_\lambda^T \cdot (f_{new} - \bar{f})$, wherein $f_{new}$ is the feature vector calculated from the current frame, $\bar{f}$ is a mean feature vector learned from a sequence of training images, and $e_\lambda^T$ is an eigenvector corresponding to a largest eigenvalue of a covariance matrix.

31. The non-transitory computer readable medium of claim 29, wherein determining a pair of training samples closest to the frame comprises:
determining a pair of training samples as:

$$\beta = \underset{j}{\operatorname{argmin}}(1 + |\mu_j - \mu_{new}|)^2 + \alpha \cdot (u_N^{(j)} - u_N^{(new)})^2$$
$$\mu_j < \mu_{new}$$

where $$\gamma = \underset{j}{\operatorname{argmin}}(1 + |\mu_j - \mu_{new}|)^2 + \alpha \cdot (u_N^{(j)} - u_N^{(new)})^2,$$
$$\mu_j \geq \mu_{new}$$

$\mu_j$ and $\mu_{new}$ are cardiac cycle values,
$u_N^{(new)}$ is a position of most proximal electrodes in u-direction, and
$\alpha$ is an empirical value.

32. The non-transitory computer readable medium of claim 31, wherein determining estimates comprises:

$\hat{m}_{new,\beta} = m_\beta + (c_N^{(new)} - c_N^{(\beta)})$; and $\hat{m}_{new,\gamma} = m_\gamma + (c_N^{(new)} - c_N^{(\gamma)})$.

33. The non-transitory computer readable medium of claim 29, wherein combining the estimates to determine a final estimate for the position of the second catheter comprises:

$\hat{m}_{new} = \phi \cdot \hat{m}_{new,\beta} + (1-\phi) \cdot \hat{m}_{new,\gamma}$, wherein
the scaling value $\phi$ between the two estimates is calculated as:

$$\phi = \frac{|\mu_\gamma - \mu_{new}|}{|\mu_\gamma - \mu_\beta|}.$$

34. The non-transitory computer readable medium of claim 29, further comprising:
compensating for the estimated cardiac and respiratory motion of the at least the portion of the heart in a 3D overlay projected onto each of the plurality of frames of the fluoroscopic image sequence.

* * * * *